(12) United States Patent
Joslin

(10) Patent No.: US 7,018,349 B1
(45) Date of Patent: Mar. 28, 2006

(54) DISPOSABLE, SIZE-ADAPTABLE ARM SLING

(75) Inventor: Marianne Joslin, Brisbane, CA (US)

(73) Assignee: FanCastic Products, Inc., Brisbane, CA (US)

(*) Notice: Subject to any disclaimer, the term of this patent is extended or adjusted under 35 U.S.C. 154(b) by 0 days.

(21) Appl. No.: 10/981,928

(22) Filed: Nov. 5, 2004

(51) Int. Cl.
*A61F 5/00* (2006.01)
(52) U.S. Cl. ............................. 602/4; 602/20
(58) Field of Classification Search ............ 602/4, 602/20, 21, 62; 2/270, 125, 111, 44, 45; 128/94, 77, 82 R, DIG. 15
See application file for complete search history.

(56) References Cited

U.S. PATENT DOCUMENTS

| | | | | |
|---|---|---|---|---|
| 2,088,927 | A * | 8/1937 | Roy | 602/4 |
| 4,285,337 | A * | 8/1981 | Cosentino | 602/4 |
| 4,622,961 | A * | 11/1986 | Christensen | 602/4 |
| 4,759,353 | A * | 7/1988 | Melendez et al. | 602/4 |
| 5,792,083 | A * | 8/1998 | Joslin | 602/4 |
| 6,102,877 | A * | 8/2000 | Joslin | 602/4 |
| 6,770,044 | B1 * | 8/2004 | Joslin | 602/4 |

* cited by examiner

Primary Examiner—Henry Bennett
Assistant Examiner—Shumaya B. Ali
(74) Attorney, Agent, or Firm—Townsend and Townsend and Crew LLP

(57) ABSTRACT

A disposable, size-adaptable arm sling for supporting a patient's arm and hand has an elongated pouch for receiving the arm therein. The pouch has an open top and open front end and a closed bottom and closed aft end and is made of a mat of at least partially fused together synthetic fibers. A multiplicity of spaced-apart, elastic strands are attached to the mat and extend in a longitudinal direction of the pouch from the aft end to the front end thereof. The elastic strands have a length when in their relaxed state which is less than the length of the pouch when in use, and the mat has a greater length than the length of the strands in their relaxed state so that the mat is stretchable in a longitudinal direction of the pouch to about the original length of the mat. A strap is affixed to the aft end of the pouch, and a hand loop attached to the pouch adjacent the front end thereof can be engaged by a portion of the patient's hand. A releasable connection is provided between a free end of the strap and the pouch adjacent the front end thereof. To apply the sling, the pouch is longitudinally stretched, thereby correspondingly elastically lengthening the strands so that the patient's arm can be placed in the pouch and his hand in the hand loop to thereby lengthen the pouch to correspond to a supported length of the patient's arm.

28 Claims, 4 Drawing Sheets

DISPOSABLE, SIZE-ADAPTABLE ARM SLING

BACKGROUND OF THE INVENTION

Arm slings are routinely used by a large segment of the population for supporting arms in a comfortable, generally horizontal position next to the person's chest during healing following injuries, surgery or due to other causes.

Such arm slings are typically worn for a relatively short period of time, normally ranging from a few days to a few weeks. Although arm slings can be reused, that is typically not the case because the person using the sling rarely has a use for it again later on.

Slings currently available are primarily constructed of a rigid fabric, such as canvas, which forms a pouch into which the arm can be placed and which has variously configured straps for placement over the wearer's shoulder to support the pouch, and the arm resting therein closely adjacent to the wearer's chest.

It has been recognized that prior art arm slings of this type have drawbacks. Canvas is relatively stiff and rough and, therefore, engages and applies pressure against high points and surfaces on the arm. Such pressure can cause discomfort or outright pain, particularly if the high points are in the vicinity of wounds or injuries along the arm. More specifically, all arm slings made of inflexible fabric create pressure points at the elbow and wrist. An inflexible arm pouch and back strap can result in uncomfortable to severe neck pain at the point where the strap crosses the neck muscle bearing the full weight of the arm.

To overcome this difficulty, the inventor has in the past devised and marketed arm slings which have arm-supporting pouches made of a soft, stretchable material, as disclosed in U.S. Pat. No. 6,770,044. The softness of the material better distributes pressure points over larger surface areas of the arm, thereby reducing potential discomfort or pain. Moreover, such slings were given a length slightly less than the length of the patient's arm so that they had to be stretched over the arm. This helps avoid the formation of folds or unevenness in the pouch, thereby contributing to alleviating uncomfortable or painful pressure points or areas.

Slings made in accordance with this patent are comfortable, practical and highly attractive. However, they are relatively expensive to produce. As a result, the use of such slings is limited to persons willing and able to afford them. Due to the relatively high price, the slings are not widely used by persons requiring only a short-term arm support, or by cost-conscious institutions, emergency rooms and the like, because insurance companies will typically limit reimbursements for arm slings to the cost of the lowest priced slings available on the market, mainly the earlier discussed, widely used slings made out of canvas and canvas-like materials.

There is therefore a current need for an arm sling which provides the benefits of the sling disclosed in U.S. Pat. No. 6,770,044 but which can be produced at a cost so that it is cost-competitive with the low-priced arm slings in the market, namely arm slings made out of the canvas and canvas-like materials.

BRIEF SUMMARY OF THE INVENTION

The present invention provides an arm sling intended for only short-term use, such as a few days to a few weeks, which avoids the formation of undesirable pressure points along the arm of the patient wearing the sling in a manner similar to the manner disclosed in the above-referenced patent, but which can be produced at a cost that makes it price-competitive to other prior art slings, e.g. slings made of canvas, without exhibiting the drawbacks of such slings. This is attained by constructing the sling of a relatively thin but sufficiently strong, low-cost material in the form of mats made of fuseable or meltable, petroleum-based polymer materials which are appropriately fused together. Such material is widely used in disposable diapers. Strands of latex-free, natural rubber elastic material are suitably attached in a uniform horizontal orientation to the fibrous mat while in their stretched state so that the mats become contracted when the strands return to their relaxed state, thereby giving the mats an undulating or shriveled-up exterior while enabling them to be lengthened (by stretching the elastic strands) to fit the sling onto the arm of the patient.

When applied to an arm, the sling of the present invention avoids the formation of pressure points, thereby enhancing the patient's comfort and preventing unnecessary pain.

As is discussed throughout this application, the fibers of the mats are synthetic fibers that can be fused together, e.g. by partially or completely melting them, or only softening them, so that, at ambient temperature, the fibers are attached or connected to each other. For purposes of this application, the word "fused" is used to describe (and claim) heat-meltable or softenable fibers which have been heated to above their softening point so that, upon cooling, the fibers become connected.

In a preferred embodiment of the invention, the elastic strands are stretched by at least about 50% while they are being attached to the fibrous mat, and preferably they are stretched 100% or more of their length in the relaxed state. As a result, the sling can be stretched and lengthened by up to twice its original length (when the elastic strands are relaxed), and one sling can be used on patients having varying arm lengths. According to one embodiment of the invention, a single-size sling, having an average length (about midway between the bottom and the top of the pouch) from its aft end to its fore end of about 12 inches, is used on patients for which at least three different sling sizes (small, medium and large) are needed when the slings are made of a rigid fabric such as canvas. This allows a reduction in the inventory that must carried by suppliers of the sling, makes certain that a sling of the proper size is available and need not be searched for (for example in emergency situations) and, therefore, saves costs while making the sling more user-friendly, particularly for persons, e.g. physicians or emergency room workers, who must retrieve and apply the slings to patients.

In one embodiment of the present invention, the disposable, size-adaptable arm sling has a pouch with a closed bottom, a closed aft end, and an open top and open front end into which the patient's arm is placed so that the elbow rests against the aft end and the patient's hand is at the front end of the pouch. The front end includes a hand loop attached to the pouch and formed so that it can be engaged by the patient's arm, and the portion of the hand between the thumb and the index finger engages the hand loop to thereby maintain the pouch in its stretched state and at a length that precisely corresponds to the length of the patient's arm, whatever it may happen to be.

The sling further has a longitudinally elastic strap made of similar but preferably more densely embedded latex-free, natural rubber material than the pouch material. One end of the strap is attached to the closed aft end of the pouch, and the other, free end is releasably connected to the open front end of the pouch. This is preferably done by extending a short strap segment, preferably a part of the hand loop, beyond the open top of the pouch, affixing a button thereto, and providing the free end of the strap with slit-like openings that can be engaged by the button. By providing a plurality of longitudinally spaced-apart slits in the strap, the length of the strap can be stretched and adjusted to the size of the wearer while providing a secure, mechanical connection. The stretchable strap provides the wearer additional comfort by allowing the arm to move somewhat naturally in the vertical direction as the wearer walks and moves about.

At least the pouch, and preferably also the strap, is constructed of the earlier mentioned mat formed of non-woven, fused-together fibers. A multiplicity of substantially parallel, elastic strands are secured to the mat and extend over substantially the full length thereof, that is, from the closed aft end to the open front end of the pouch. The strands have a length when in their relaxed state which is no more than about two-thirds of the length of the mat and preferably lie in the range between two-thirds and one-half (50%) of the length of the mat to provide the desired stretchability.

Since the elastic strands in the mat also provide tension strength (in the longitudinal direction of the strands) and the strap must carry the entire weight of the arm, which can exceed 35 pounds for large-size persons, the density of the strap (defined by the spacing between the strands) is greater in the strap than in the pouch. The strands are elastomeric rubber bands of a diameter expressed as a denier/dtex range of between about 650 to about 900 and preferably of about 750 dtex, and their spacing in the mats of the pouch is in the range between about 5 to 10 mm, while the corresponding spacing between the elastic strands in the strap is in the range of only between about 2 to 4 mm.

When the pouch and the strap are made of a material such as the earlier mentioned petroleum-based polymer, the mats are soft to the touch, moisture-absorbent, air-permeable and, therefore, comfortable even when in direct contact with the patient's skin. In addition, the pouch and the strap are both resilient in their longitudinal directions, which absorbs shock and therefore makes them more comfortable to wear.

Moreover, such mat materials are readily assembled by fusing the mats, strap and other components to each other, that is, by applying heat along desired seams, which sufficiently softens or partially melts the fibers so that, upon cooling, they form strong seams capable of withstanding the loads to which the sling is subjected during use. In addition, during the assembly of the mat, all parts thereof, that is, the two panels which are assembled into the pouch of the sling, the strap and the hand loop, can be placed flat and parallel against and over each other. Once in proper alignment, the parts can be quickly assembled by applying heat along the seam where the parts are to be adhered to each other, thereby fusing the fibers of the mat and forming a seam at very low cost. In a preferred embodiment of the invention, the seams are formed so that they resist spreading any tears that may form in the sling, thereby extending the lifetime of the sling.

While the comfort afforded by the sling of the present invention is of greater significance to the patient, the low cost with which the sling can be produced is of utmost importance to providers of the sling. Low-cost prior art slings, typically hand-sewn together from non-disposable material, can cost five times as much as the sling of the present invention, which can be produced of inexpensive, disposable material with automated equipment able to produce thousands of units daily which require no hand-sewing. This 5:1 cost advantage of the present invention virtually assures that the sling will be widely accepted because it is substantially as comfortable as the most expensive slings presently on the market, yet it costs less than the least expensive but relatively most uncomfortable, as well as unattractive, slings that are currently available. Thus, the sling of the present invention is truly disposable due to its low manufacturing costs.

DESCRIPTION OF THE PREFERRED
EMBODIMENTS

Figure 1:
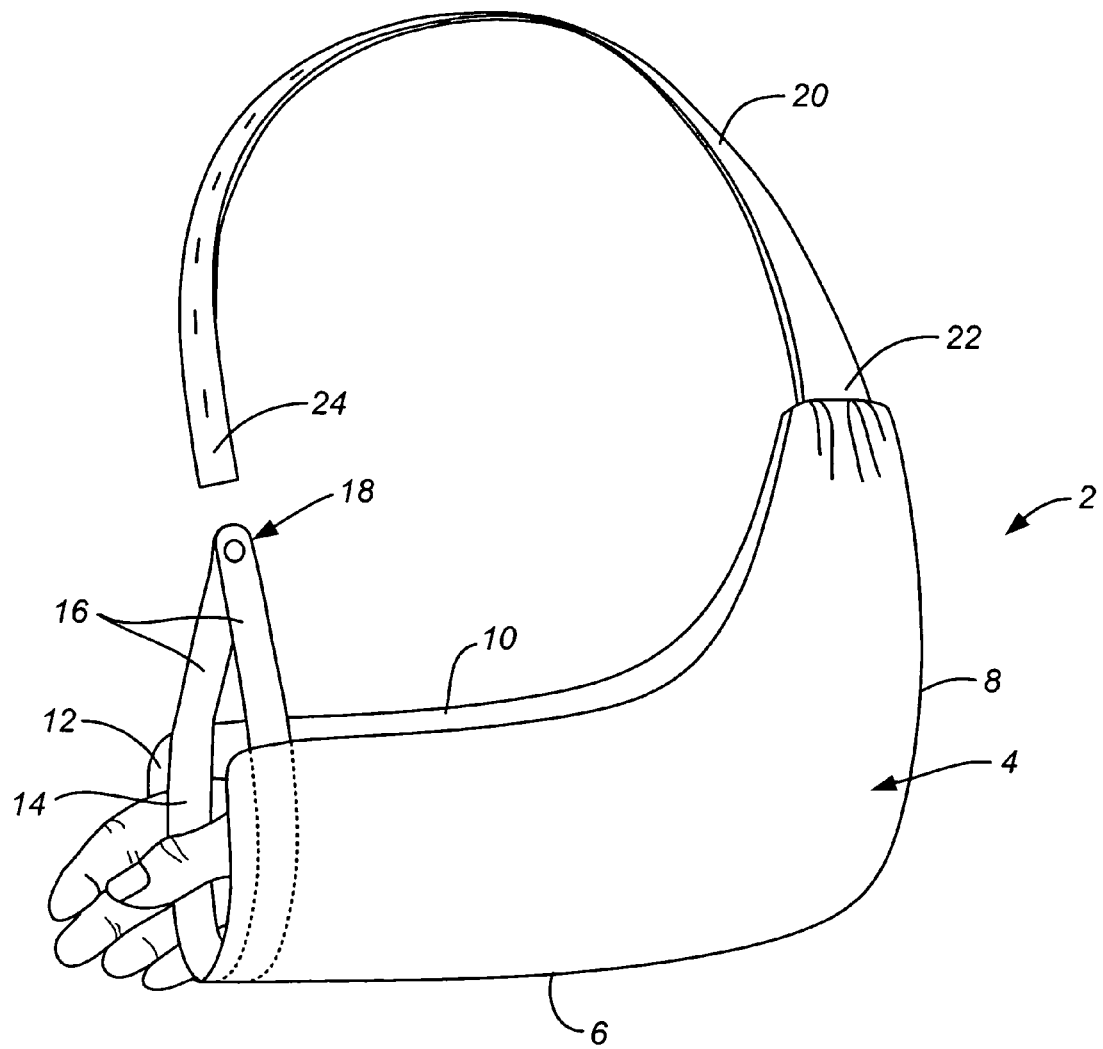
FIG. 1 is a perspective elevational view showing it applied over the hand and arm of a patient.

Referring to FIG. 1, the sling 2 of the present invention has a pouch 4 with a closed bottom 6, a closed aft end 8, an open top 10 and an open front end 12. At the front end, the sling includes a hand loop 14 which is appropriately fixed to and located on the inside of the pouch, as is further described below, and which preferably has a section 16 projecting along each side of the pouch past the open top end thereof to a connecting point 18. A strap 20 has a first end 22 which is secured to the aft end of the pouch and a second, free end that is releasably connected to the projecting sections of the hand loop, as is further described below.

Figure 2:
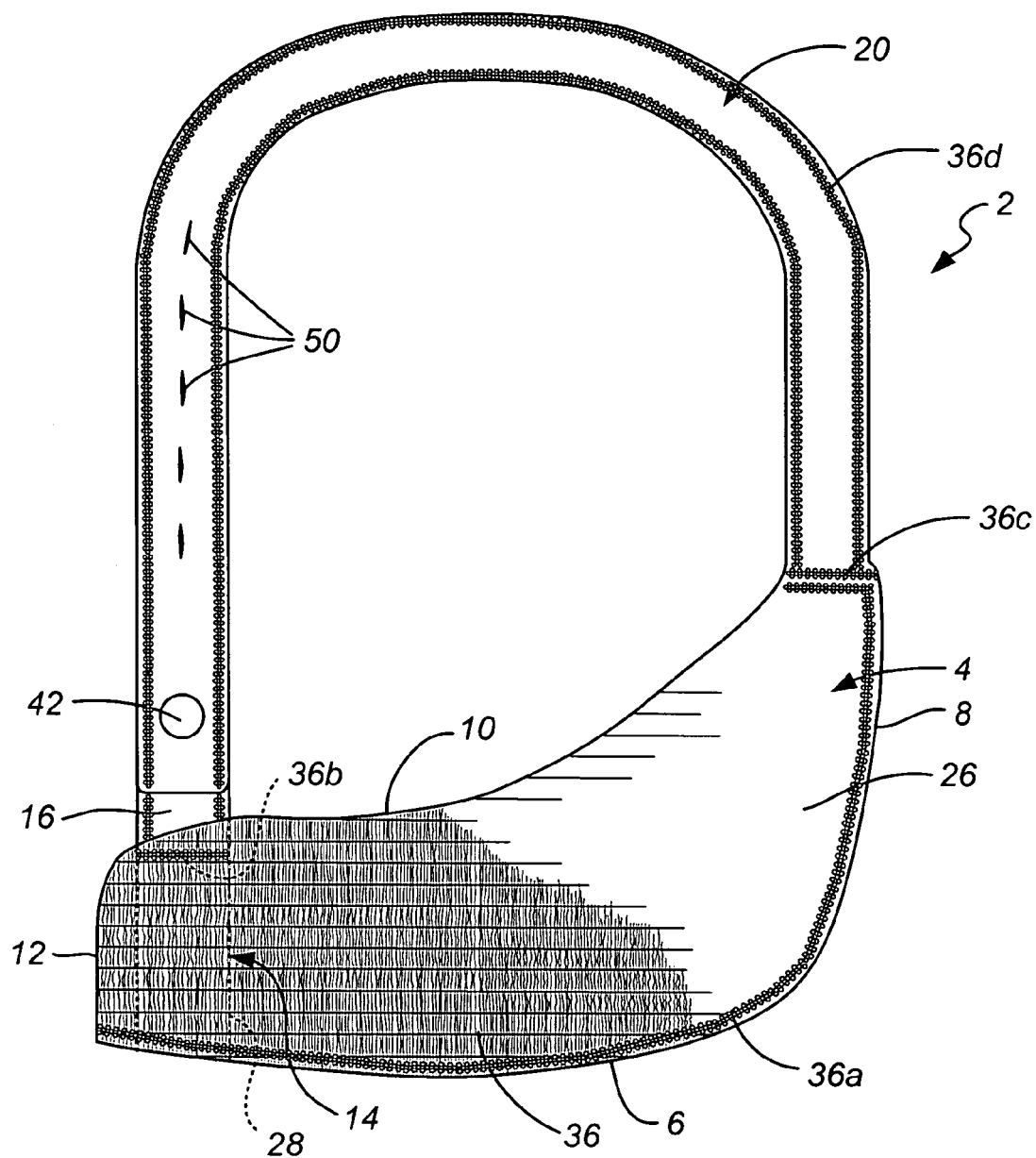
FIG. 2 is a side elevational view of the sling in its assembled but relaxed state.
Figure 3:
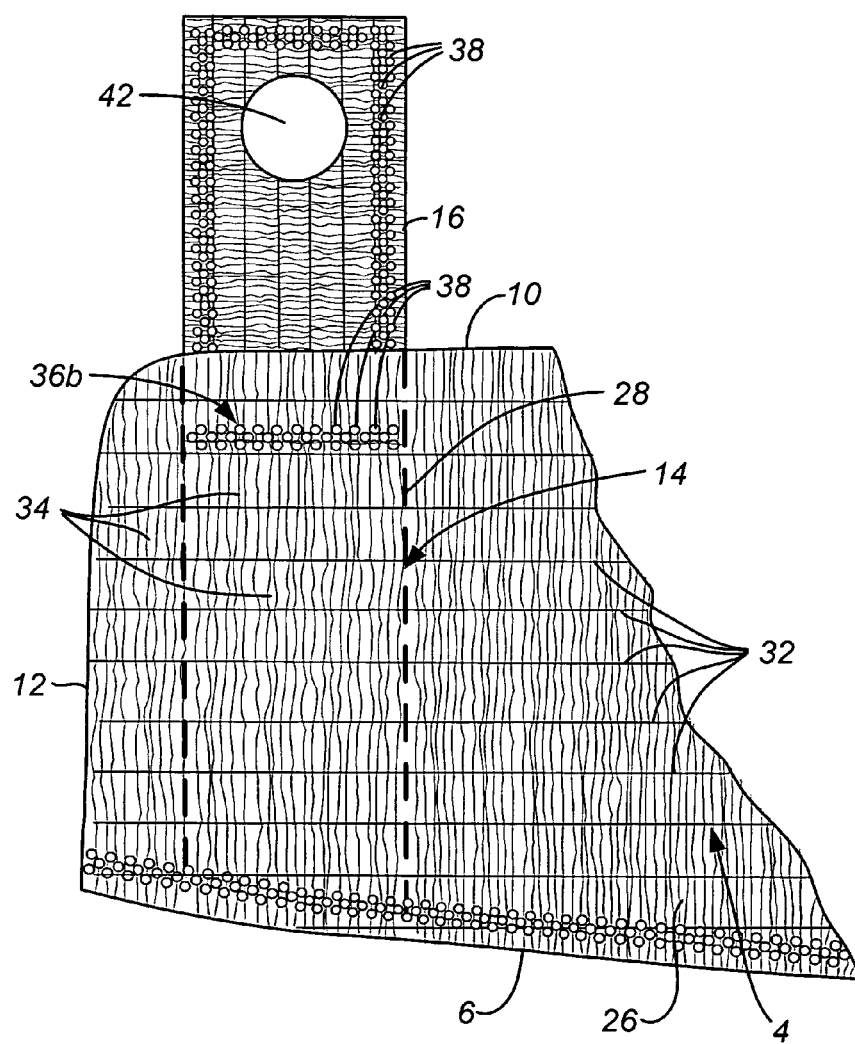
FIG. 3 is an enlarged, fragmentary side elevational view of the front end of the sling.
Figure 4:
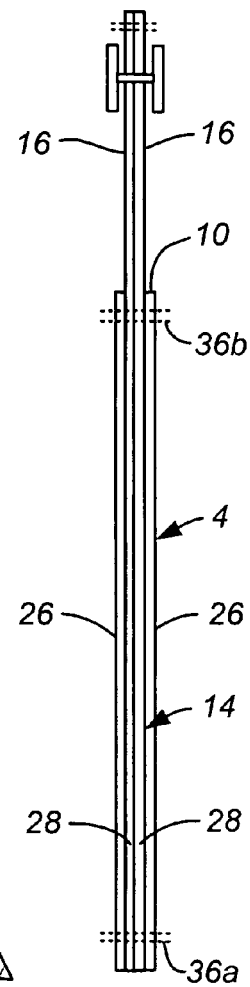
FIG. 4 is a front elevation of the sling shown in FIG. 3.
Figure 5:
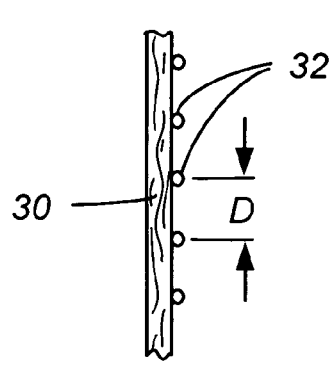
FIG. 5 is an enlarged, fragmentary, cross-sectional view illustrating the matted material of which the sling can be constructed.
Figure 6:
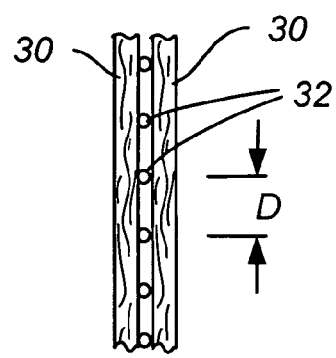
FIG. 6 is a view similar to FIG. 5 and illustrates an alternative material for the sling.
Figure 7:
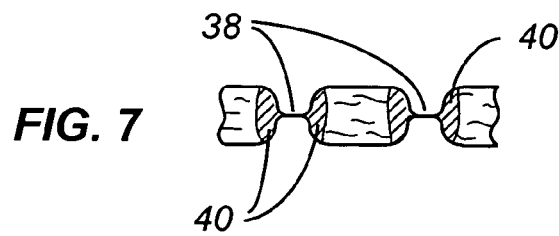
FIG. 7 is an enlarged, fragmentary, cross-sectional view through a portion of a fused seam connecting parts of the sling.

Referring now to FIGS. 2–6, pouch 4 of the sling is constructed of two identically shaped panels 26 which are flat and placed on top of each other, as is illustrated in FIG. 2. Hand loop 14 is formed by two flat bands 28, which are sandwiched between the pouch panels as can be seen in FIG. 4. The hand loop bands extend from the closed bottom 6, where they are attached, e.g. fused, to the pouch, and extend in the form of projecting loop sections 16 past the open top 10 of the pouch. The hand loop is preferably also made of a mat of fuseable synthetic fibers so that the hand loop can be fused to the pouch.

Panels 26 are made from a mat of fibers made of a heat-softening, meltable plastic material, preferably the earlier mentioned petroleum-based polymer. The fibers are normally randomly distributed over the surface area of the mat and secured or attached to each other by applying heat (and thereby softening or partially melting the fibers) so as to fuse them together. Attached to the mat are elongated strands of an elastic material, preferably latex-free natural rubber, which extend substantially parallel to the length of the pouch from the aft end 8 to the front end 12. The elastic strands are spaced apart by a distance "D", which, as earlier stated, is preferably in the range between 5 to 12 mm. In one embodiment of the invention, illustrated in FIG. 5, the elastic bands are attached to one side of mat 30, for example by spraying or otherwise applying a flexible bonding agent over the strands and the mat. In another embodiment of the invention, shown in FIG. 6, the elastic strands 32 are sandwiched between two opposing fiber mats 30. The strands can be secured to the mats with a bonding agent or by applying heat to the two mats so that they become fused to each other and thereby lock the strands in place.

Before the elastic strands are secured to the mats, the strands are stretched to increase their length by between about 50% to 100%, or more, from their length in their relaxed state. The strands are secured (e.g. bonded) to the mats while stretched. Thereafter, the strands are released and they will contract to their original, relaxed length. This shortens the length of the pouch between the aft and front ends by the same amount by which the stretched strands contract. Resulting excess mat material (in the longitudinal direction) forms irregular undulations 34, as is schematically illustrated in FIG. 3.

As a result of this construction, the pouch is stretchable, in a longitudinal or horizontal direction of the pouch. However, it is not stretchable in the perpendicular vertical direction.

In a preferred embodiment of the invention, the pouch is constructed so that it has a length between the closed aft end and the hand loop 14 which is less than the length of the arm of any person expected to wear the sling. In a presently preferred embodiment, this distance averages about 12 inches (it is somewhat longer at the top of the pouch and shorter at the bottom of the pouch because the aft end of the pouch slightly slopes in the vertical direction as is shown in the drawings) for a sling adapted to fit most adults. As the pouch is stretched, to elongate it for applying it over the arm of a patient, the surface undulations of the mats gradually disappear.

Sling 2 is assembled by first cutting out pouch side panels 26 from a mat 30 while the elastic strands 32 thereof are in their relaxed state. The two panels are positioned flat against each other, and two hand loop bands 28 are placed between them adjacent the front end 12 of the sling.

Further, first end 22 of strap 20 is placed between the overlying pouch panels adjacent the aft ends 8 thereof so that the flat sides of the strap lie flat against the panels of the pouch. Strap 18 is constructed of a fibrous mat, including initially stretched and thereafter relaxed elastic strands in the same manner in which side panels 26 of the pouch are constructed. The main difference between the strap material and the pouch material is that the strap preferably has a greater elastic strand density "D"; i.e. the elastic strands in the strap are more closely spaced than the strands of the pouch, as is illustrated in FIG. 3, because the elastic strands provide tensile strength and flexible vertical weight-bearing capability crucial to patient fit and comfort.

This construction of the strap renders it longitudinally stretchable so that the strap somewhat resiliently suspends the pouch, which provides added comfort for the wearer of the sling.

Returning to the assembly of the sling, the panels, strap and hand loop bands are secured or "fused" to each other by applying heat along desired seams 36a–d (shown in FIG. 2) by causing a softening or melting of the fibers in the mat, for example with a hot roll, a stamp with a heated lip having the outline of the desired seam, and the like.

To prevent a spreading of tears that may form in the fiber mats, the seams are preferably formed by forming holes or thin, weakened depressions 38 while the fibers are being fused together. As a result, fibrous material displaced by the holes or depressions agglomerates around the periphery of the holes or depressions and, upon cooling, forms reinforcements 40 about the holes/depressions which resist tearing and also a spreading of tears in the mats. To enhance the strength of the seam and further help prevent the spreading of tears, the seam holes or depressions 38 are preferably arranged in two or more substantially parallel rows with holes or depressions 34 in the rows being offset from each other or staggered as is illustrated in FIG. 3.

Figure 8:
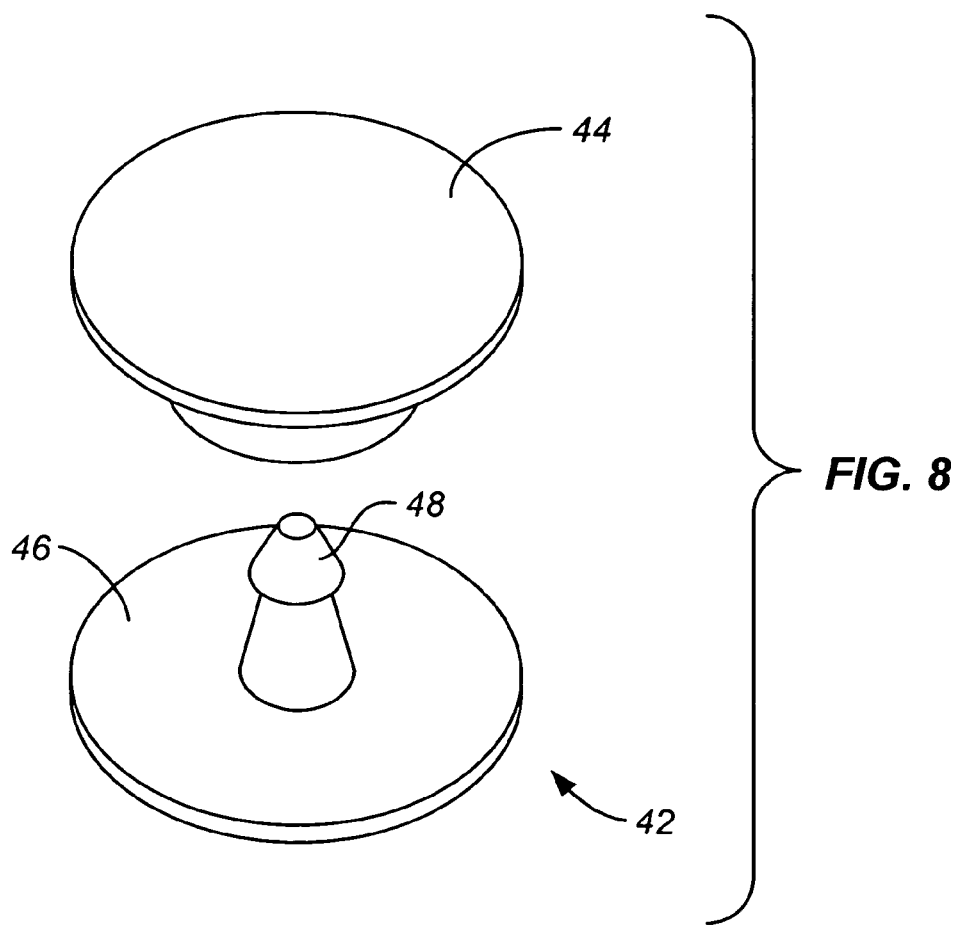
FIG. 8 is an exploded, enlarged view of a button constructed in accordance with the present invention for releasably securing one end of a carrying strip of the sling to the pouch of the sling.

To attach the free end 24 of strap 20 to the protruding hand loop sections 16, a double-sided button 42 (shown in detail in FIG. 8) is secured to the ends of the hand loop sections. The button is preferably constructed of a relatively hard plastic material in the form of two button halves 44, 46, one of which includes a projection 48 that can be snapped into a corresponding hole (not shown in the drawings) in the other half to lock the two halves to each other. The button projection 48 is inserted into a hole (not separately shown) at the free end of the projecting hand loop section 16 and becomes affixed thereto when the other button half is snapped onto the projection. The distance between the opposing inside surfaces of the button is sufficiently large so that one or the other button half can be engaged with one of several longitudinally spaced-apart slits at the free end 24 of the strap. The slits are oriented parallel to the length of the strap so that they do not spread apart when weight is attached to the strap, and further so that their formation does not sever any of the elastic strands in the strap. By providing several longitudinally spaced slits, the effective length of the strap can be varied by inserting the button in the strap slit, which provides the desired strap length.

To apply sling 2 to the arm of a patient, pouch 4 is initially opened and slipped over the patient's arm so that his/her elbow (including a lower portion of the upper arm) engages the closed aft end 8 of the pouch. The pouch is pulled in a forward direction to lengthen it, by correspondingly stretching elastic strands 32, so that the back of the patient's hand is between the inside of one of the pouch panels 26 and the adjacent hand loop 14 while his thumb is on the outer side of the hand loop. The stretched pouch is now released, and the resiliency of elastic strands 32 retracts the front end of the pouch rearwardly until the hand loop comes to rest between the patient's thumb and remaining fingers, thereby fitting the pouch to the precise length of the patient's arm (as measured from between the thumb and the fingers to his/her elbow), irrespective of the actual length thereof.

Strap 20 is then looped and thereby hung over the patient's neck and shoulder, and the free end 24 is aligned with button 42 while the pouch rests against the patient's chest at the desired elevation. The button is now inserted in the appropriately positioned slit 50 of the strap to complete the application of the sling to the patient's arm. Any excess length of the strap can be cut off with scissors to avoid a loosely dangling strap end and enhance the appearance of the sling.

It will be noted that the sling can be applied to either hand of the patient since hand loop 14 is symmetrical about the center line of the pouch (see FIG. 4).

What is claimed is:

1. A size-adaptable arm sling for supporting an arm from an elbow to a hand thereof comprising a pouch with a closed bottom and aft end and an open top and front end for placing the arm therein so that the elbow engages the closed aft end and the hand is at the open front end of the pouch, a hand loop attached to the pouch proximate the front end and defining at least one opening through which at least a portion of the hand can be extended, a strap having a first end attached to the pouch proximate the aft end thereof and a second end, means for attaching the second end of the strap to the pouch proximate the open front end, the pouch having a length from the closed aft end to the opening and being constructed of a mat formed of non-woven fibers, and a multiplicity of substantially parallel elastic strands secured to the mat and extending over substantially the full length of the mat from the closed aft end to the open front end, the strands having a length in their relaxed state which is less than the length of the pouch so that, when the strands are in their relaxed state, a distance between the closed aft end and the opening is less than the length of the pouch.

2. A size-adaptable arm sling according to claim 1 wherein the strap is constructed of a mat formed of non-woven fibers secured to each other and a multiplicity of substantially parallel elastic strap strands secured to the mat of the strap, the strap strands extending over substantially the full length of the mat between the first and second ends of the strap, the strap strands having a length when in their relaxed state which is no greater than about 75% of a length of the strap.

3. A size-adjustable arm sling according to claim 2 wherein a density of the elastic strands in the strap is greater than a density of the elastic straps in the pouch.

4. A size-adjustable arm sling according to claim 1 wherein the opening is in part formed by an inner side of the pouch.

5. A size-adaptable arm sling according to claim 4 wherein the pouch has opposing, spaced-apart side walls defining the open top, and including a hand loop attached to the inner sides of the side walls, a section of which projects past the open top of the side walls, and wherein the means for attaching the second end of the strap to the pouch includes the portion of the hand loop and the second end of the strap.

6. A size-adaptable arm sling according to claim 5 wherein the attaching means comprises a button secured to one of the portion of the hand loop and the second end of the strap and a button-engaging hole adapted to receive the button formed in the other one of the portion of the hand loop and the second end of the strap.

7. A size-adaptable arm sling according to claim 6 wherein the button is secured to the portion of the hand loop and wherein the strap includes a plurality of longitudinally spaced-apart apertures for receiving the button while permitting adjustment of the length of the strap by engaging the button with different apertures in the strap.

8. A size-adaptable arm sling according to claim 7 wherein the aperture is located between adjacent strands of the strap.

9. A size-adaptable arm sling according to claim 8 wherein the apertures define slits substantially parallel to the strands in the strap.

10. A size-adaptable arm sling according to claim 1 wherein the pouch is constructed of two flat panels of the mat and the fibers are made of a heat-meltable material, and including a seam connecting the panels along the aft end and the bottom of the pouch formed by fusing the fibers of the mat to each other.

11. A size-adaptable arm sling according to claim 10 wherein the seam is formed by a multiplicity of closely adjacent, spaced-apart weakened portions of the mat surrounded by fibers which are fused together to prevent a spreading of tears in the seam.

12. A size-adaptable arm sling according to claim 11 including additional seams for securing the first end of the strap and the hand loop to the pouch, the additional seams having the same structure as the seam.

13. A size-adaptable arm sling according to claim 1 wherein the mat forms an undulating mat surface when the elastic strands are in their relaxed state.

14. A size-adaptable arm sling for supporting an arm from an elbow to a hand comprising a pouch formed by flat, abutting panels constructed of a non-woven mat of fuseable synthetic fibers, the panels forming a bottom, a top and aft and front ends of the pouch, and a seam extending along the aft end and the bottom of the pouch formed by fibers located along the seam which have been fused together, each panel including a multiplicity of spaced-apart elastic strands which extend from the aft end to the front end of the pouch, are secured to fibers of the mat, and have a length in their relaxed state which is substantially less than the length of the panels so that the panels form an undulating surface when the strands are in their relaxed state and the pouch can be lengthened by stretching it in its longitudinal direction to adapt its size to the size of an arm to be placed therein, a hand loop attached to sides of the panels facing each other, the loop being attached to the panels proximate the bottom and the top of the pouch to define openings between each panel and the hand loop through which a portion of the hand can be extended, the hand loop including a connecting section which extends past the top of the pouch, a strap constructed of a mat of fuseable synthetic fibers connected to each other, the strap having flat sides which are arranged substantially parallel to the panels of the pouch, a first end attached to the panels proximate the aft end of the pouch and a second, free end, the strap including a plurality of substantially parallel, spaced-apart elastic strands which have a length less than a length of the mat of the strap when the strands are in their relaxed state so that the length of the strap is less than a length of the mat of the strap when the strands are in their relaxed state, and a connection between the free end of the strap and the connecting section of the hand loop comprising a button secured to the connecting section and a plurality of longitudinally spaced-apart openings in the strap formed to engage the button so that an effective length of the strap can be adjusted by engaging the button with different openings in the strap, connections between the strap, the panels of the pouch and the hand loop being formed by portions of the fibers in the mat of the pouch, the mat of the strap and the hand loop which are fused together.

15. A size-adaptable arm sling according to claim 14 wherein the hand loop is constructed of a material including fuseable synthetic fibers.

16. A size-adaptable arm sling according to claim 14 wherein the openings in the strap comprise slits in the mat of the strap which extend in a longitudinal direction of the strap.

17. A size-adaptable arm sling according to claim 14 wherein a density of the elastic strands in the strap is greater than a density of the elastic strands in the pouch.

18. A size-adaptable arm sling according to claim 14 wherein the strands in the panels of the pouch have a length in their relaxed state which is no greater than about two-thirds of the length of the panels.

19. A size-adaptable arm sling according to claim 14 wherein a length of the strands in the panels of the pouch in their relaxed state is no greater than about 50% of the length of the panels of the pouch.

20. A size-adaptable arm sling according to claim 14 wherein the strands comprise latex-free natural rubber strands.

21. A size-adaptable arm sling according to claim 14 wherein the fibers of the panels and the mat comprise a petroleum-based polymer material.

22. A size-adaptable arm sling according to claim 14 wherein the elastic strands are bonded to the panels and the mat.

23. A size-adaptable arm sling according to claim 14 wherein the panels of the pouch are constructed of first and second fibers sheets arranged face to face and the strands are sandwiched between and secured to the sheets.

24. A size-adaptable arm sling according to claim 20 wherein the first and second fiber sheets are fused together.

25. A size-adaptable arm sling according to claim 24 wherein the strands are secured at least intermittently over their length to at least one of the first and second fiber sheets.

26. A size-adaptable arm sling according to claim 14 wherein the length of the strands of the panels in their relaxed state is no greater than about two-thirds of a length of the panels.

27. A size-adaptable arm sling according to claim 14 wherein the length of the strands of the panels in their relaxed state is no greater than about one-half of a length of the panels.

28. A method of supporting an arm of a patient with a size-adaptable arm sling comprising producing an elongated pouch for receiving the arm therein, the pouch having an open top and open front end and a closed bottom and closed aft end and being made of a mat of at least partially fused together synthetic fibers and a multiplicity of spaced-apart, elastic strands attached to the mat and extending in a longitudinal direction of the pouch from the aft end to the front end thereof, the elastic strands having a length when in their relaxed state of no more than about 12 inches, the mat having a length at least about one-third greater than the length of the strands in their relaxed state so that the mat has an undulating surface and is stretchable in a longitudinal direction of the pouch to about the length of the mat, a strap affixed to the aft end of the pouch, a hand loop attached to the pouch adjacent the front end thereof which can be engaged by a portion of the hand, and a releasable connection between a free end of the strap and the pouch adjacent the front end thereof, placing an elbow of the patient's arm into the pouch and engaging the elbow with the closed aft end of the pouch, stretching the pouch in a longitudinal direction by correspondingly elastically lengthening the strands, placing a portion of the patient's hand in the hand loop to thereby lengthen the pouch to correspond to a supported length of the patient's arm, selecting a desired length for the strap for adequately supporting the patient's arm in the sling, closing the connection between the free end of the strap and the pouch, and hanging the strap over the patient's shoulder to thereby support the patient's arm with the arm sling.

* * * * *